US007341865B1

(12) United States Patent
Norris et al.

(10) Patent No.: US 7,341,865 B1
(45) Date of Patent: Mar. 11, 2008

(54) LIQUID DELIVERY DEVICES AND METHODS

(75) Inventors: Michael Norris, Santa Clara, CA (US); Mark Trulson, San Jose, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 834 days.

(21) Appl. No.: 10/304,566

(22) Filed: Nov. 26, 2002

Related U.S. Application Data

(60) Provisional application No. 60/421,267, filed on Oct. 25, 2002.

(51) Int. Cl.
*C12M 3/00* (2006.01)

(52) U.S. Cl. .............................. 435/287.2; 435/288.3; 435/288.4; 422/100; 422/104

(58) Field of Classification Search .................... None
See application file for complete search history.

(56) References Cited

U.S. PATENT DOCUMENTS 5,948,685 A * 9/1999 Angros ........................ 436/63
6,040,193 A * 3/2000 Winkler et al. ............. 436/180
6,395,536 B2 * 5/2002 Freeman .................. 435/286.5
6,594,432 B2 * 7/2003 Chen et al. ................. 385/133
6,732,574 B2 * 5/2004 Hajduk et al. ............. 73/54.05
6,755,131 B2 * 6/2004 Dannoux et al. ........... 101/485
2002/0048754 A1 * 4/2002 Lockhart et al. ............... 435/6
2002/0142483 A1 10/2002 Yao et al.
2003/0143725 A1 * 7/2003 Chen et al. .............. 435/287.2
2003/0224505 A1 * 12/2003 Patno et al. ............. 435/287.2
2005/0153096 A1 * 7/2005 Gerber et al. ................. 428/85

OTHER PUBLICATIONS

Zarrinkar, P. et al., "Arrays of Arrays for High-Throughput Gene Expression Profiling" *Genome Research* 11, 1256-1261 (2001).

* cited by examiner

*Primary Examiner*—David Redding
(74) *Attorney, Agent, or Firm*—Deanna A. Arnold

(57) ABSTRACT

Methods and devices are provided for using high-density arrays of diverse chemical entities. In preferred embodiments, small volumes of multiple liquids are delivered to multiple reaction sites on a single substrate where the liquids are constrained to localized reaction sites. The substrate need not be cut apart prior to being used for analysis. Accordingly, the area of the substrate on which analysis may be performed is maximized. In many embodiments of the present invention, constraining regions hinder the transport of liquids between adjacent reaction sites.

11 Claims, 9 Drawing Sheets

SECTION A-A
SECTION C-C
DETAIL B
SCALE 4 : 1
120
130
202
204
205
206
209
210
215
217
220
225
230
235
240
245
249
255

LIQUID DELIVERY DEVICES AND METHODS

CROSS REFERENCE TO RELATED APPLICATIONS

The present application claims priority to U.S. provisional patent application Ser. No. 60/421,267, filed Oct. 25, 2002, entitled "Methods & Apparatus for Chemical Compound Detection", the disclosure of which is specifically incorporated herein by reference.

FIELD OF THE INVENTION

The invention relates to diverse fields that involve the nature of molecular interaction, including chemistry, biology, microarray technology, medicine and diagnostics. This invention relates more specifically to methods for performing diverse assays on a substrate with very small amounts of reactants. This invention also specifically relates to methods for performing microarray assays.

BACKGROUND OF THE INVENTION

Microarray technology has developed to analyze a large number of complex biochemical reactions and systems in parallel. This technology provides a massively parallel form of analysis that increases data collection per unit time, decreases the overall time required for analysis, and uses smaller sample volumes. For these and other reasons, microarray technology is well suited for genomic research.

A microarray is a collection of chemical entities arranged on a substrate, which substrate is often glass, fused silica, borosilicate, quartz, soda lime glass, or some such similar substance. Each chemical entity occupies a predetermined position on the substrate. These positions are often referred to as "features", "probes" or "probe regions" and may contain one to millions or more copies of a single chemical entity. These chemical entities may be of any number of classes of substances including, but not limited to nucleic acids, peptides, polysaccharides, carbohydrates, and phospholipids. After exposing the microarray to a sample under selected test conditions, scanning devices can examine locations in the microarray to determine whether sample molecules have interacted with probe regions at those locations.

Microarrays with a large number of probe regions may be manufactured by methods described in PCT Application WO 92/10092 or U.S. Pat. Nos. 5,143,854; 5,384,261; 5,405,783; 5,412,087; 5,424,186; 5,445,934; 5,744,305; 5,800,992; 6,040,138; 6,040,193, all of which are hereby incorporated by reference in their entireties for all purposes. The probe regions may have side dimensions from about 10 μm to 100 μm. In some embodiments a probe region may be larger, such as about 1 cm across. In some applications, the substrate is a wafer with a synthesis area of about 110 mm×110 mm and may include large numbers of probe regions.

Wafers contain probe regions arranged in a plurality of probe arrays, such that each probe array comprises a specific subset of probe regions and is physically separated from the adjacent probe array(s). Typically, wafers containing the probe arrays are cut apart and packaged prior to being used for analysis. Therefore, probe arrays are separated by inert areas, commonly known as "alleys," which allow space for a saw or similar tool to make cuts between the probe arrays. Each alley is commonly about 3 mm wide. Accordingly, the area occupied by alleys can be a significant part of the total area of a wafer, thereby reducing the area that may be used for probe arrays. Further, dicing and packaging probe arrays is expensive and wastes expensive substrate. However, it allows a plurality of samples to be tested on probe arrays produced from a single wafer.

It would be desirable to perform analyses with a plurality of samples on whole wafers, thereby avoiding the cost and wasted material involved with dicing and packaging probe arrays. However, if the wafer is not physically cut apart prior to analysis, other devices and methods are needed to isolate reaction sites on whole wafers.

SUMMARY OF THE INVENTION

Methods and devices for utilizing high-density arrays are provided by virtue of the present invention. In preferred embodiments, small volumes of multiple liquids are delivered to multiple reaction sites on a single substrate. The liquids may contain nucleic acids, peptides, polysaccharides, phospholipids, hybrid polymers, glycoproteins, inorganic compounds, proteins, peptides, antibodies, carbohydrates, acids, bases, salts, compounds, buffers, or solvents. Because the substrate need not be cut apart prior to being used for analysis and does not require fluidically separate chambers to isolate reaction sites, the size of the regions between reaction sites can be minimized.

According to some embodiments of the present invention, an apparatus is provided for introducing liquids to a plurality of areas on a substrate. The apparatus includes a first ("dry") chuck for retaining the substrate in a predetermined position and a second ("wet") chuck having a first side configured to receive a liquid and to constrain the liquid to a selected area of the substrate. The first side may include a plurality of raised portions, each of which corresponds with a selected area of the substrate, and a plurality of grooves separating the raised portions.

According to other embodiments of the present invention, the raised portions may be hydrophilic and the surfaces of the grooves may be hydrophobic. In certain embodiments of the invention, the apparatus further includes the substrate. In other embodiments, the first chuck contains channels to retain the substrate by reducing the atmospheric pressure between the substrate and the first chuck. In still other embodiments, the second chuck has a second side that has a channel extending from the second side to the first side. This channel may be used to deliver a liquid to the first side of the second chuck, which is proximal to a selected area of the substrate. In this way, the liquid may be contacted with and constrained to the predetermined region of the substrate. In some embodiments, the flow of the liquid through the channel is facilitated by capillary action, gravity flow, or a pressure differential. In other embodiments, the invention further comprises a manual or automated fluid-handling device, and the channel is configured to receive liquid from the fluid-handling device.

In many embodiments, the first and second chucks are configured such that when assembled with a substrate a gap is maintained between the substrate and the raised portions of the second chuck. In related embodiments, a channel from the second side of the second chuck to the first side of the second chuck is used to deliver a liquid to the gap between the substrate and the raised portions of the second chuck.

In some such embodiments, the selected areas on a substrate are probe arrays and the second chuck constrains the a liquid to predetermined probe arrays. In some such embodiments, the areas on the substrate are probe regions and the second chuck constrains the a liquid to predetermined probe regions. In other embodiments, a selected area may be more than one probe array or more than one probe region and the second chuck constrains the a liquid to the selected area. Probe arrays may contain many different kinds of probes, such as nucleic acid probes or polypeptide probes. Often, the liquid applied to a substrate contains a substance that will interact with chemical entities present on the substrate.

In certain embodiments, the invention also includes a substrate frame that positions and retains the substrate on the first chuck. This substrate frame may also be configured to engage with the second chuck. Further, this substrate frame may be configured to engage with a washing apparatus. In some embodiments, the first chuck has pins that extend from the first chuck and engage with and position the second chuck. These pins may also pass through a substrate frame such that they position and hold the substrate frame.

In some embodiments, a first side of a wet chuck includes a series of grooves or "canyons" which surround and define "mesas" corresponding to reaction sites on a substrate. In some such embodiments, the canyons correspond with alleys between reaction sites on the substrate. In some such embodiments, a plurality of channels known as "micro-wells" extend from a top surface of the wet chuck to mesas of the wet chuck, allowing reactant to be introduced to the probe arrays through a second side of the wet chuck, preferably when the mesas are proximate the reaction sites. Accordingly, the canyons help to prevent the flow of contaminants between mesas, and thus between reaction sites, as well.

According to some embodiments of the present invention, each mesa of the wet chuck has a first shape that conforms to a second shape of a corresponding reaction site. Moreover, each of the mesas is preferably bounded by a canyon having a third shape that conforms to a fourth shape of the corresponding alleys surrounding the reaction site. In such embodiments, the canyons and corresponding alleys define constraining regions that confine a liquid to the corresponding reaction site.

In some methods according to the present invention, a substrate is aligned on a dry chuck in a first step. In preferred aspects of the invention, the alignment step includes optically aligning the substrate according to markings on the dry chuck and/or the substrate. A first surface of the substrate includes reaction sites bounded by alleys. In a second step, the substrate is mounted on a dry chuck. In some preferred aspects of this method, the substrate is mounted by evacuating air between the dry chuck and a second surface of the substrate. In a third step, mesas formed on a first side of a wet chuck are placed proximate the reaction sites of the substrate. In a fourth step, predetermined quantities of one or more liquids are introduced to the reaction sites via micro-wells in a second side of the wet chuck. According to some aspects of this method, the fourth step includes introducing liquids through the micro-wells via a robotic pipettor or other automated delivery system. According to one aspect of the present invention, the fourth step includes the steps of introducing a first liquid to a first reaction site, introducing a second liquid to a second reaction site, introducing a third liquid to a third reaction site, and continuing until n liquids have been introduced to n reaction sites.

According to some aspects of the present invention, a method is provided for constraining liquids to a selected area of a substrate. The method includes the steps of dispensing a liquid on a mesa of a wet chuck and placing the mesa in proximity to the selected area of the substrate, thereby wetting the selected area of the substrate with the liquid and constraining the liquid to the selected area of the substrate. The invention further contemplates simultaneously constraining a plurality of liquids to selected areas of a substrate. The method includes transferring each liquid to an individual mesa of a wet chuck and placing the mesas in proximity to the selected areas of the substrate, thereby wetting the selected areas of the substrate and constraining the liquids to the selected areas of the substrate. According to some embodiments, the transfer of a liquid to a mesa of a wet chuck occurs through a micro-well in the wet chuck.

According to some aspects of the present invention, a method is provided for constraining a first liquid to a first area of a substrate and a second liquid to a second area of the substrate. The method includes the steps of: dispensing the first liquid through a first micro-well in a first side of a wet chuck to a first raised portion in a second side of the wet chuck; dispensing the second liquid through a second micro-well in the first side of the wet chuck to a second raised portion in the second side of the wet chuck; constraining the first liquid to the first area of the substrate by holding the first raised portion of the second side of the wet chuck in proximity to the first area of the substrate; and constraining the second liquid to the second area of the substrate by holding the raised portion of the second side of the wet chuck in proximity to the second area of the substrate. According to some such aspects of the invention, the first and second liquids contain substances that are selected from the group consisting of polynucleotides, polypeptides, polysaccharides, phospholipids, hybrid polymers, glycoproteins and inorganic compounds. In certain embodiments, the dispensing steps are performed with a fluid-handling system configured to deposit the first liquid in the first micro-well and the second liquid in the second micro-well.

The invention further contemplates a method for conducting reactions on a substrate comprising a substrate having chemical entities bound on a first surface, dispensing at least one liquid onto a known location of said first surface of said substrate, said liquid being limited to the known location. Said chemical entities may include, but are not limited to polynucleotides, polypeptides, polysaccharides, phospholipids, glycoproteins, hybrid polymers, and inorganic compounds.

BRIEF DESCRIPTION OF THE DRAWINGS

The following figures form part of the present specification and are included to demonstrate certain aspects of the patent invention. The invention may be better understood by reference to one or more of these drawings in combination with the detailed description of the specific embodiments presented herein.

DETAILED DESCRIPTION OF THE INVENTION

General

Figure 1:
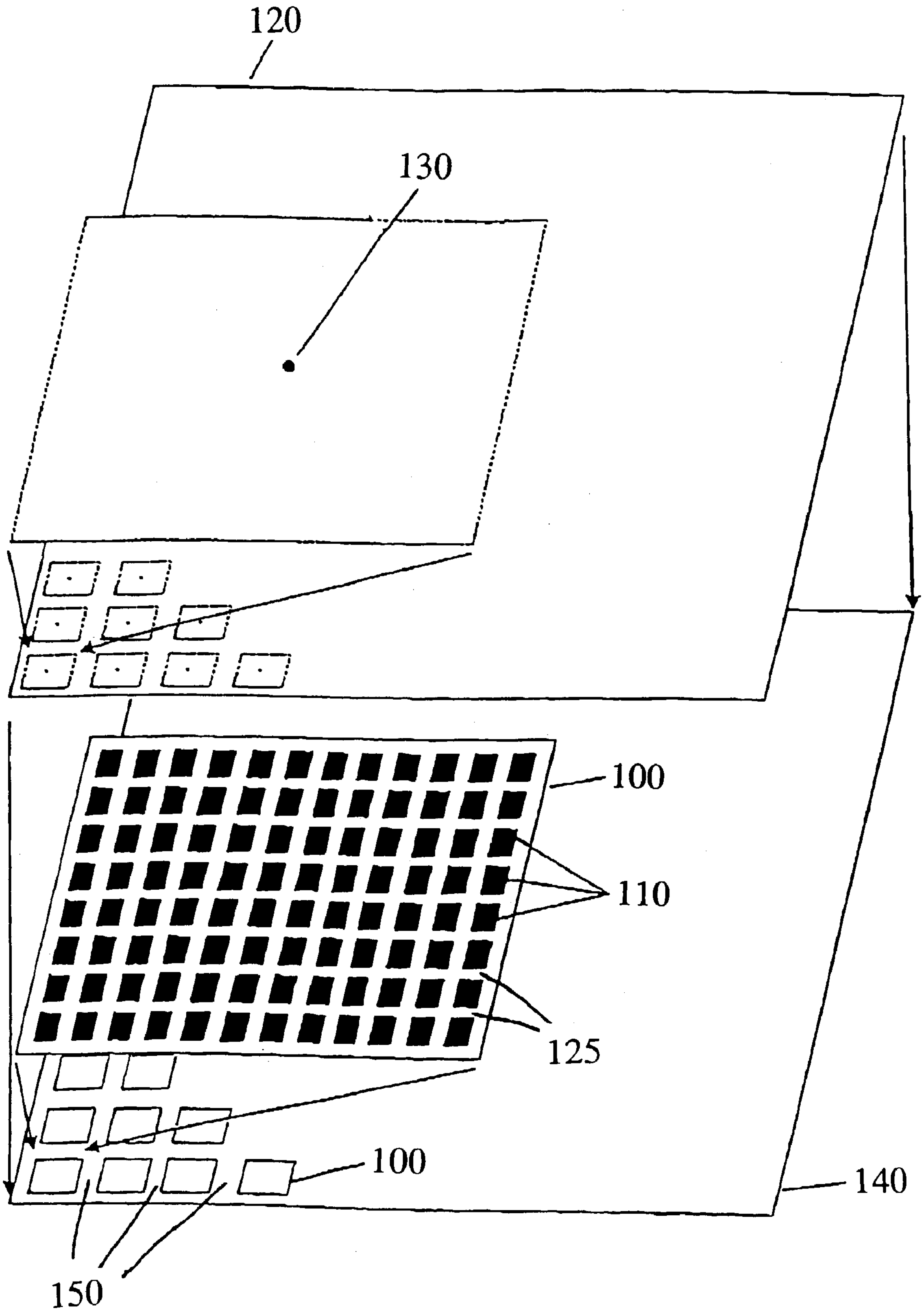
FIG. 1 depicts probe regions and probe arrays disposed on a substrate and the corresponding parts of a wet chuck according to one embodiment of the present invention.

The present invention relies on patents, applications and other references for details known to those of skill in the art. Therefore, when a patent, application, or other reference is cited or repeated below, it should be understood that it is incorporated by reference in its entirety for all purposes as well as for the proposition that is recited.

As used in the specification and claims, the singular forms “a,” “an,” and “the” include plural references unless the context clearly dictates otherwise. For example, the term “an agent” includes a plurality of agents, including mixtures thereof.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as “from 1 to 6” should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Very Large Scale Immobilized Polymer Synthesis (VLSIPS™) has enabled the rapid and automated synthesis of microarrays, or probe arrays, that are smaller than a thumbnail containing hundreds of thousands or more different chemical entities. These probe arrays have been produced in which each location has a scale of, for example, ten microns. The probe arrays can be used to determine whether a sample molecule interacts with any of the probe regions on the probe array. After exposing the probe array to a sample molecule under selected test conditions, scanning devices can examine each location in the probe array and determine whether a sample molecule has interacted with the probe region at that location. U.S. patent application Ser. No. 09/922,492, filed Aug. 3, 2001, entitled “High Performance Wafer Scanning” discloses such scanning devices and is incorporated herein by reference in its entirety for all purposes.

Probe arrays are useful in a variety of screening techniques for obtaining information about either a probe region or a sample molecule being applied to the probe region. For example, a library of peptides can be used to generate a probe array such that each probe region contains a plurality of copies of a single peptide, and such a probe array may be used to screen for drugs. In one such embodiment, the peptides can be exposed to a receptor, and those probe regions (containing peptides, in this case) that bind to the receptor can be identified.

Probe arrays containing nucleic acid probe regions can be used to extract information from, for example, nucleic acid samples. A nucleic acid sample is exposed to a probe array under conditions that allow hybridization. The array is then scanned to determine to which probe regions in the probe array the sample nucleic acid has hybridized. One can obtain information by careful selection of samples and probe regions, and using algorithms to compare patterns of hybridization and non-hybridization. This method is useful for investigating the gene expression patterns of cells, among other uses. Such methods are described, for example, in U.S. patent application Ser. No. 10/106,097, filed Mar. 26, 2002, U.S. patent application Ser. No. 10/042,819, filed Jan. 7, 2002, U.S. patent application Ser. No. 10/152,404, filed May 21, 2002, and U.S. patent application Ser. No. 10/134,510, filed Apr. 29, 2002, which are incorporated herein by reference in their entirety for all purposes.

There are additional methods for manufacturing probe arrays and the present invention in not limited to any one method. U.S. Pat. No. 6,040,193 describes alternate methods, which include spotting, presynthesized nucleic acids on substrates, the use of flow channels, constraining means and other techniques. PCT application No. 99/00730 (WO 99/36760), entitled “Depositing Fluid Specimens on Substrates, Resulting Ordered Arrays, Techniques for Analysis of Deposited Arrays,” which is incorporated by reference, describes an unique spotting method involving a pin and ring device that accurately places precise volumes of liquids on substrates.

In a preferred embodiment of the present invention, a substrate containing a plurality of probe arrays will handle small volumes of multiple samples simultaneously. Generally, a sample is prepared, probe arrays are exposed to the sample, and then the probe array is analyzed. The current invention addresses the need for using very small samples, which, in some cases, may eliminate gene amplification techniques (such as polymerase chain reaction) as a normally required step of analysis. Faster reaction time and more efficient sample use are advantageous in large-scale genome projects. The present invention allows one to conduct many assays simultaneously on a single substrate while consuming small volumes of samples.

Although the invention is particularly applicable to use delivering samples to wafers, it is more generally applicable to any method in which a small volume of a liquid is to be delivered to a substrate and constrained to a specific region of the substrate. Typically, the specific region of the substrate, often called a "reaction site", contains a chemical entity that may interact with a substance present in the liquid. The invention includes the placement of a liquid directly on the substrate through the use of a device that channels a sample to a specific location and restricts the sample to that specific location, thus allowing, for example, a plurality of samples to be applied to the same substrate. The specific location may be, for example, a single probe array or a plurality of probe arrays. Further, a variety of reactions or assays may be performed on a substrate using the methods described herein, including, but not limited to hybridization, polymerization, and digestion. Others will be readily apparent to those of skill in the art.

I. SAMPLE PREPARATION

In the context of the present invention, a liquid to be applied to a substrate may contain one or more unknown or known substances, for example, nucleic acids, proteins, peptides, antibodies, or derivatives thereof, phospholipids, polysaccharides, hybrid polymers, glycoproteins, inorganic compounds, carbohydrates, acids, bases, salts, compounds, buffers, solvents or other reactants. The liquid may further be a solution, mixture, or a pure substance. In the interest of brevity, the term "liquid" will be used to mean any such entity to be applied to a substrate according to the present invention. A liquid to be applied to a substrate may have been prepared in any number of ways well known in the art. For example, if a biological sample contains a nucleic acid, the sample may be treated in many different ways including, but not limited to, purified, amplified, labeled, fragmented, phosphorylated, dephosphorylated, subjected to restriction digestion or ligation, etc. to produce a liquid for application to a substrate. Further, if a sample contains a polypeptide, it may be treated in many different ways including, but not limited to, purified, denatured, protease-treated, labeled, phosphorylated, dephosphorylated, glycosylated, etc. to produce a liquid for application to a substrate.

Any appropriate method of sample preparation may be employed to reduce the complexity of the sample, yielding multiple, non-identical populations containing sample molecules of interest in a liquid to be applied to a substrate. Such methods of fractionation comprise separating molecules by size, mass, epitope, etc. For example, amplicons from a PCR reaction may be fractionated such that only full-length amplicons are applied to a probe array.

In one embodiment, a sample molecule in a liquid to be applied to a substrate may be generated through enzymatic digestion. For a nucleic acid sample, this may be accomplished using one or more restriction enzymes. Likewise, polypeptide samples may be subjected to treatment with one or more proteases prior to application to a probe array. Those of skill in the art will be familiar with the digestion of nucleic acids with restriction enzymes and proteins with proteases. A sample molecule in a liquid to be applied to a substrate may also or optionally be labeled with radioactive, fluorescent, or other tags prior to application to a probe array.

Nucleic acid samples include, but are not limited to, DNA, RNA, cDNA, protein nucleic acids, or nucleic acid mimetics, and may be naturally occurring or synthetic. In some embodiments, a liquid to be applied to a substrate contains genomic DNA. DNA samples are often subject to amplification before application to an array using primers flanking the region of interest. DNA may be obtained from virtually any tissue source (other than pure red blood cells), such as whole blood, muscle, buccal tissue, skin, and hair follicles. Other convenient sources of DNA include semen, saliva, tears, urine, fecal material, and sweat. Amplification of genomic DNA containing a polymorphic site generates a single species of sample nucleic acid if the individual from whom the sample was obtained is homozygous at the polymorphic site or two species of sample molecules if the individual is heterozygous. Genomic DNA may not be amplified in some circumstances. See, for example, U.S. Provisional Application Ser. Nos. 60/228,251, filed Aug. 26, 2000, and 60/228,253, filed Aug. 26, 2000, the entire teachings of which are incorporated herein by reference.

RNA samples are also often subject to amplification, which is typically preceded by reverse transcription. Amplification of all expressed mRNA can be performed, for example, as described by applications WO 96/14839 and WO 97/01603. Amplification of an RNA sample from a diploid sample can generate two species of sample molecules if the individual from whom the sample was obtained is heterozygous at a polymorphic site occurring within the region of DNA that encodes the expressed RNA. In some embodiments, a liquid to be applied to a substrate contains mRNA from one or more specific tissues of an organism.

One suitable method of amplification is polymerase chain reaction (PCR), which is described in *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); U.S. Pat. No. 4,683,202; and U.S. patent application Ser. No. 10/042,492, filed Jan. 9, 2002 (each of which is incorporated by reference for all purposes). Nucleic acids in a sample are usually labeled in the course of amplification by inclusion of one or more labeled nucleotides in the amplification mix. Labels can also be attached to amplification products after amplification (e.g., by end-labeling; see U.S. application Ser. No. 08/882,649, filed Jun. 25, 1997, hereby incorporated by reference). The amplification product can be RNA or DNA depending on the enzyme and substrates used in the amplification reaction. Commercial labeling kits can be purchased from Enzo Biochem (New York).

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), self-sustained sequence replication (Guatelli et al., *Proc. Nat. Acad. Sci. USA,* 87, 1874 (1990)), and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively. All of the above methods are hereby incorporated by reference in their entireties.

Once the liquid has been prepared, it may be applied to a probe array and then analyzed. The methods of this invention allow the application of minute liquid micro-fractions through a wet chuck onto a substrate. Because the micro-fractions may be added sequentially across the wet chuck without contamination, these methods greatly improve the efficiency and flexibility of performing assays on probe arrays. For example, more than one liquid may be applied to distinct and separate regions of a single substrate. It may also be desirable to apply a liquid to a number of probe regions or probe arrays. For example, it may be desirable to apply a liquid containing a nucleic acid to a set of probe arrays that, in combination, span the entire length of a chromosome or chromosomal region.

II. DETAILED DESCRIPTION OF THE DRAWINGS

This invention contemplates a number of devices and methods that allow multiple analyses, or assays, to be performed simultaneously on a single substrate. The analyses are performed on selected regions of the substrate, sometimes referred to herein as "reaction sites." The devices and methods of the present invention constrain a liquid to a reaction site of the substrate without requiring the reaction site to be diced from the substrate and/or separately packaged. Further, this invention does not require a physical barrier between adjacent reaction sites to create fluidically separate chambers as a way to isolate reaction sites, as described in U.S. Pat. Pub. App. No. 20020048754, Ser. No. 09/682,838, filed Oct. 23, 2001, incorporated herein in its entirety for all purposes.

FIG. 1 is a schematic view of one embodiment of the invention. Substrate 140 includes a plurality of probe arrays 100 separated by alleys 150. Each probe array 100 includes a plurality of probe regions 110 separated by interstitial regions 125. Although probe arrays 100 depicted in FIG. 1 are rectangular and substantially uniform in size, probe arrays 100 may have any convenient shape or size.

Probe regions can be of any size or shape that is desired or preferred, and may be arrayed in a variety of ways on a substrate. For example, they may be arranged in probe arrays 100 on a substrate. In some applications, a substrate 140 may contain large numbers of probe arrays 100, and in other applications there may only be a few or a single probe array. Likewise, a probe array may contain many or a few probe regions, depending on the requirements for carrying out a desired function. A substrate 140 may also have probe regions that are not organized in probe arrays, or may have other formats, as well.

Wet chuck 120, shown as a simple plane in this figure, includes a micro-well 130, shown as a dot in this figure, which is a channel to deliver a liquid to a selected region of substrate 140. This selected region is sometimes referred to herein as a "reaction site." In some embodiments, wet chuck 120 includes a micro-well 130 for each probe array 100, although FIG. 1 is simplified such that only one micro-well 130 corresponding to one probe array 100 is shown. In other embodiments, wet chuck 120 includes a micro-well 130 for each probe region 110. In yet other embodiments, wet chuck 120 includes a single micro-well 130 for selected groups of probe regions 110 or probe arrays 100. In still other embodiments, wet chuck 120 does not include micro-wells 130.

Micro-well 130 may also be used to remove a liquid from regions of substrate 140. Preferably, at least some portions of wet chuck 120 are formed of a material that is at least slightly hydrophilic. Such materials include, but are not limited to glass, silicon, silica, metals treated to be non-reactive and plastic or acrylic that has been roughened. In some preferred embodiments of the present invention, wet chuck 120 includes a pattern of hydrophilic portions corresponding to reaction sites on substrate 140 and hydrophobic portions corresponding to alleys 150 or interstitial regions 125. The hydrophilic or hydrophobic nature of these regions of the wet chuck may be an intrinsic property of the material from which the wet chuck was made, or may be due to further treating the regions or coating them with hydrophilic or hydrophobic substances, respectively.

Wet chuck 120 is placed in contact with, or very near to, the surface of substrate 140. In some embodiments, the separation between the wet chuck 120 and substrate 140 is between 0.003 inches and 0.01 inches. The wet chuck can be attached to the substrate by any attachment means known in the art, for example, gluing (e.g., by ultraviolet-curing epoxy or various sticking tapes), acoustic welding, sealing (e.g. by reducing the air pressure between wet chuck 120 and substrate 140), clamping, magnetic force, electrostatic force, or by relying on the weight of wet chuck 120.

Figures 2, 2A, 2B, 2C, 2D:
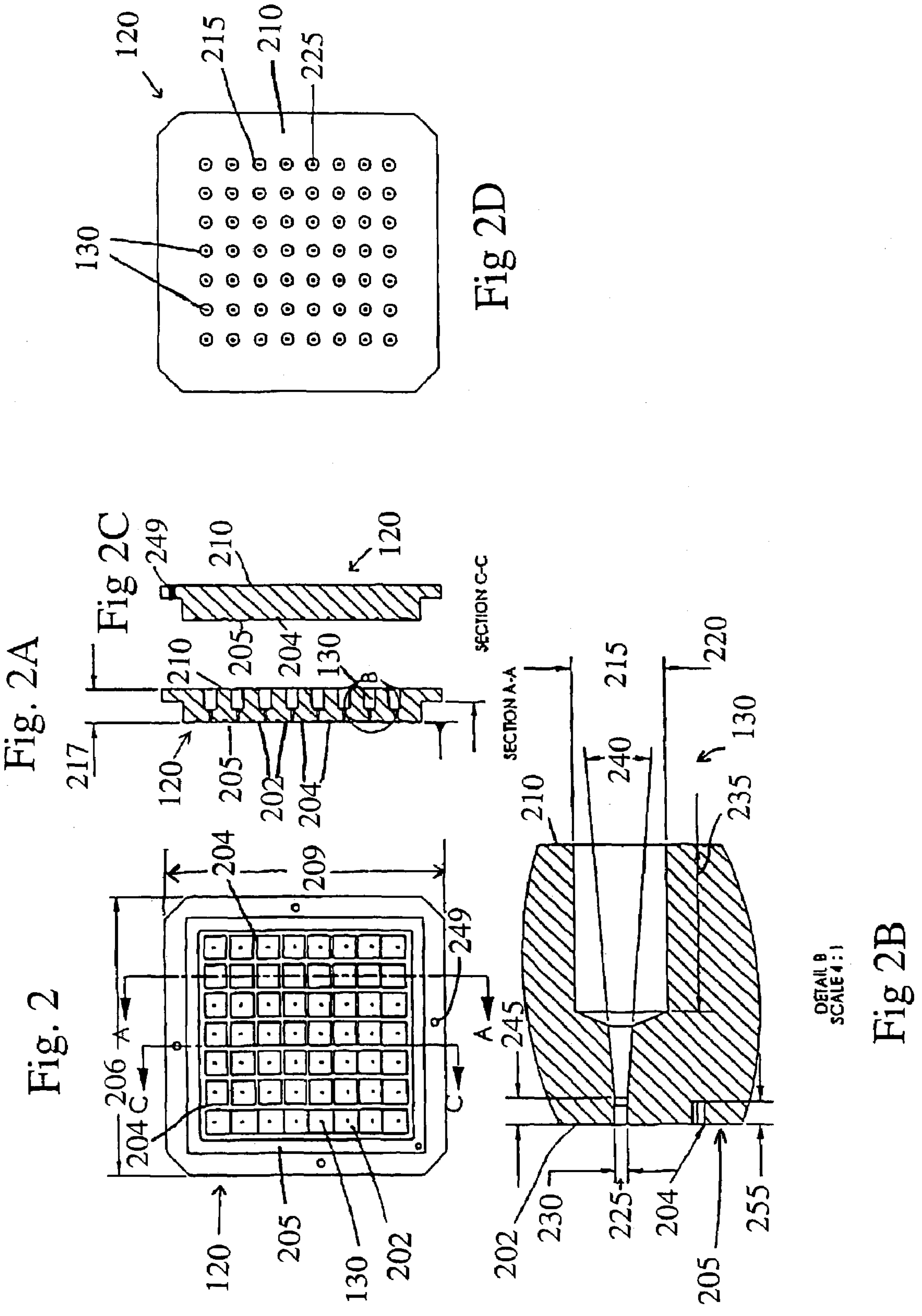
FIG. 2 is a bottom view of a wet chuck according to one embodiment of the invention.
FIG. 2A is a cross-section through mesas of a wet chuck according to one embodiment of the invention.
FIG. 2B is a cross-section through a micro-well of a wet chuck according to one embodiment of the invention.
FIG. 2C is a cross-section through a canyon of a wet chuck according to one embodiment of the invention.
FIG. 2D is a top view of a wet chuck according to one embodiment of the invention.

FIG. 2 illustrates side 205 of wet chuck 120 according to one embodiment of the present invention. Width 206 may be any convenient width. In some exemplary embodiments, width 206 is 2 inches or less; in other embodiments, width 206 is 10 inches or more and in yet other embodiments width 206 is between 2 and 10 inches. In the embodiment shown in FIG. 2, length 209 is approximately equal to width 206, but in other embodiments length 209 and width 206 are substantially different. Moreover, while wet chuck 120 is roughly square in the embodiment shown in FIG. 2, wet chuck 120 may be formed into any convenient shape.

Figure 8:
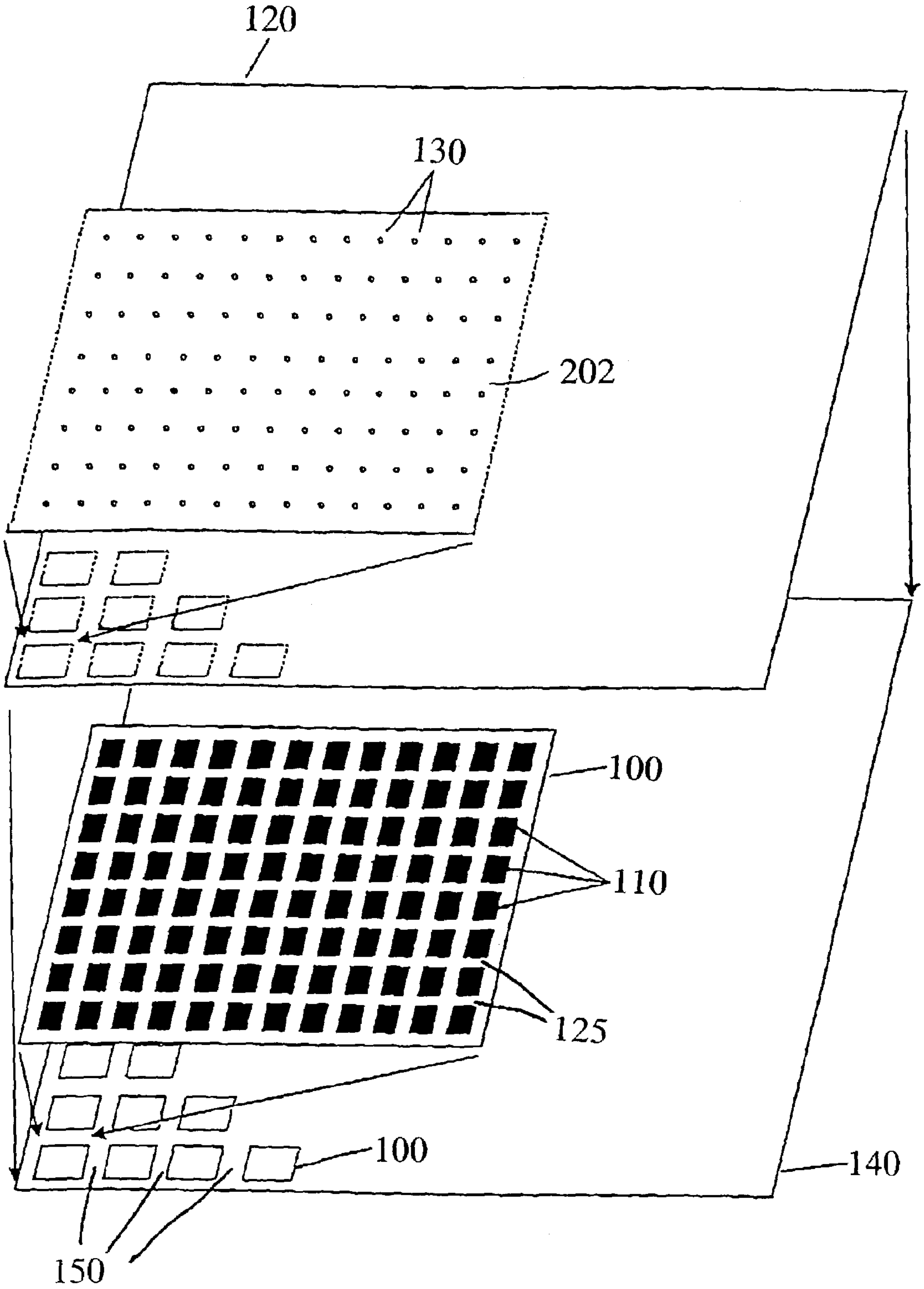
FIG. 8 depicts probe regions and probe arrays disposed on a substrate and the corresponding parts of a wet chuck according to an alternative embodiment of the present invention.

Side 205 is configured to face substrate 140. In this embodiment, each raised area or "mesa" 202 of side 205 is penetrated by a single micro-well 130. In some embodiments, each of mesas 202 includes a plurality of micro-wells 130, as shown in FIG. 8. In other embodiments, mesas 202 do not include any micro-wells 130. In preferred embodiments in which there is one micro-well per mesa, the micro-well is approximately centered in the micro-well, and hence approximately centered over the reaction site. In preferred embodiments in which there are more than one micro-well per mesa, the micro-wells are arranged approximately evenly throughout the micro-well, and hence approximately evenly over the reaction site.

A mesa 202 is disposed near a reaction site of substrate 140 and tends to keep a liquid proximate the reaction site. For the purpose of brevity, such a mesa is said to "correspond to" such a reaction site. In certain embodiments, the shape of the mesa is identical to (or slightly larger than) and aligned with a reaction site, thereby completely covering the reaction site without overlapping an adjacent reaction site. In some embodiments, each edge of the mesa extends 50 microns further than the reaction site. In preferred embodiments of the present invention, liquid applied to the substrate 140 via the corresponding mesa 202 is constrained to the entire area of a single reaction site and does not flow to an adjacent reaction site. Grooves or "canyons" 204 separate mesas 202 and act as capillary stops between such reaction sites, such that liquid applied to one reaction site does not seep into adjacent reaction sites. In some embodiments, the reaction sites comprise individual probe arrays 100. In other embodiments, the reaction sites comprise groups of probe arrays 100. In still other embodiments, the reaction sites comprise probe regions 110 or groups of probe regions 110.

As noted above, in some embodiments probe arrays are one or more centimeters on a side: therefore, in such embodiments reaction sites may have areas of several square centimeters or more. However, some probe regions are on the order of 10 microns across: in such embodiments, reaction sites may have areas of approximately 100 microns. In preferred embodiments, the alleys 150 or interstitial regions 125 that separate such reaction sites are at least partially hydrophobic. The hydrophobicity of these alleys may be an intrinsic property of the material from which the substrate was made, or may be due to further treatment or coating the alleys with a hydrophobic substance.

In some embodiments, the number and shape of mesas 202 and the widths and locations of canyons 204 correspond with the numbers and shapes of reaction sites on substrate 140. The wet chuck of FIG. 2 has 56 mesas and therefore is configured to isolate up to 56 reaction sites. In some such embodiments, the 56 corresponding reaction sites comprise individual probe arrays 100 which are separated by alleys 150 varying in width from 1 mm to 3 mm and the corresponding canyons 204 have widths in the same range. In some embodiments, hundreds, thousands or even tens of thousands of mesas 202 are formed on an individual wet chuck and the dimensions of canyons 204 are correspondingly smaller.

However, smaller mesas do not necessarily correspond to smaller canyons, nor do larger mesas necessarily correspond to larger canyons. In some embodiments, relatively large mesas may be separated by relatively small canyons. Mesas and canyons may be of any size that will constrain the liquid to a particular reaction site on the substrate.

Figures 4, 4A, 4B, 4C, 4D:
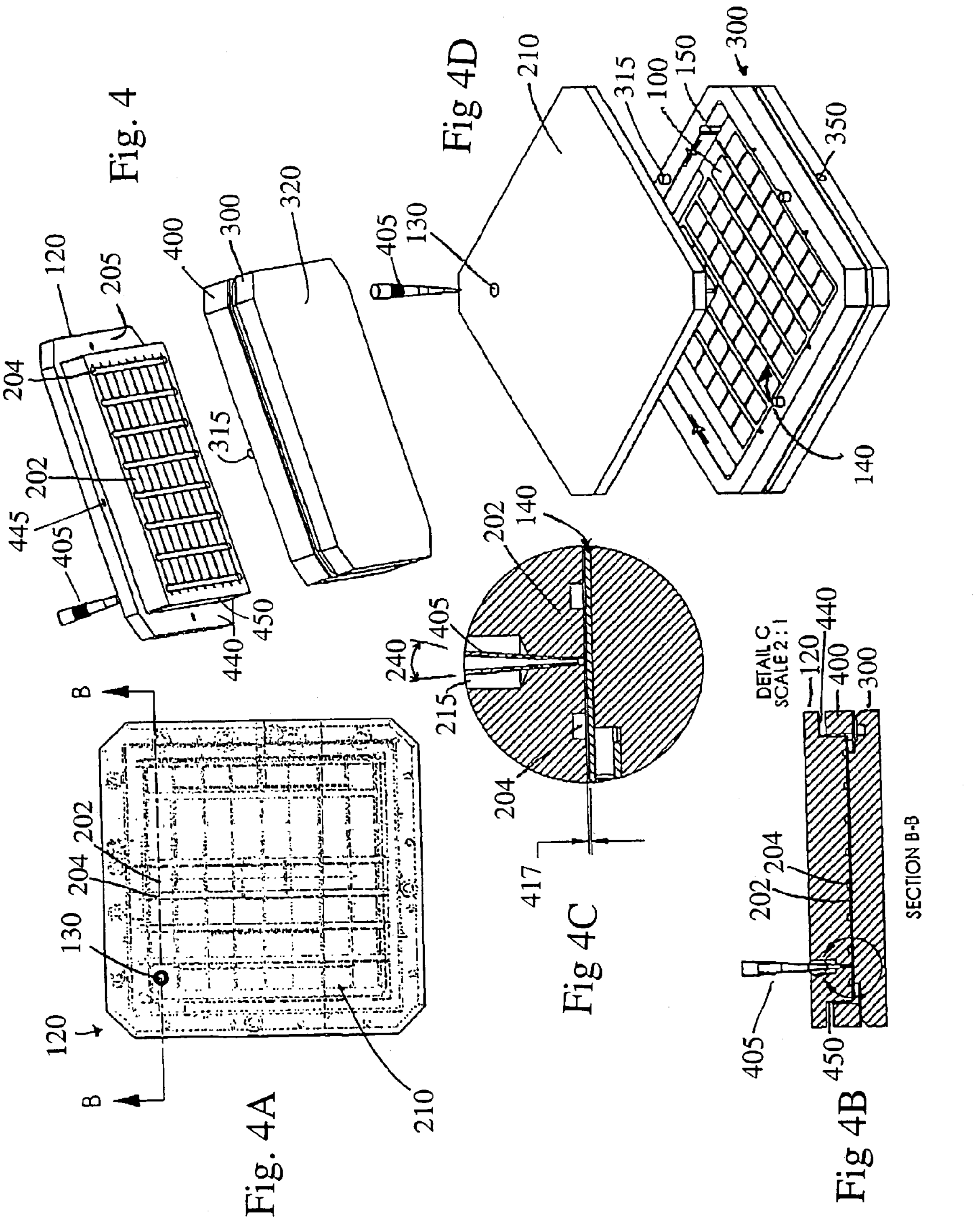
FIG. 4 is a exploded view of a wet chuck and a dry chuck according to one embodiment of the invention.
FIG. 4A is top view of a wet chuck according to one embodiment of the invention.
FIG. 4B is a cross-section through an assembled wafer, wet chuck and dry chuck according to one embodiment of the invention.
FIG. 4C is an enlarged view of a part of the a cross-section of FIG. 4B.
FIG. 4D is a second exploded view of a wet chuck and a dry chuck according to one embodiment of the invention.

In some embodiments, the widths and depths of canyons 204 may depend on the size of gap 417 between wet chuck 120 and substrate 140. Gap 417 is illustrated in FIG. 4C. If gap 417 is small, the widths and depths of canyons 204 may be made correspondingly small, in part because the volume of liquid to be contained is also small. For example, if gap 417 is approximately 25 microns, canyons 204 may be approximately 100 microns wide and slightly more than 25 microns deep, especially if the edge of canyons 204 is sharp.

FIG. 2A is a cross-sectional view of the wet chuck illustrated in FIG. 2 taken along line A-A, which passes through a column of mesas 202 and micro-wells 130. Exemplary dimensions of mesas 202 and canyons 204 may be seen on side 205. Micro-wells 130 penetrate wet chuck 120 from side 210 through side 205. Width 217 may be any convenient width; in some embodiments, width 217 is between 0.25 inches and 1.5 inches.

FIG. 2B is an enlargement of circled area B in FIG. 2A, which encompasses one of micro-wells 130, one of canyons 204 and part of a mesa 202. The dimensions, spacing and configuration of these components depend on various factors, including the density of reaction sites and the intended method of introducing a liquid. In this embodiment, micro-wells 130 are configured to receive a micropipette tip from a standard, commercially available fluid-handling device, such as those available from Tecan AG. In one exemplary embodiment, opening 215 has a diameter 220 of approximately 0.25 inches, opening 225 has a diameter 230 of approximately 0.035 inches, depth 235 is approximately 0.45 inches, angle 240 is approximately 9 degrees, depth 245 is approximately 0.07 inches and depth 255 is approximately 0.06 inches. However, all of these dimensions vary substantially from embodiment to embodiment. For example, angle 240 may vary from zero degrees (constant diameter) to 45 degrees or more. Moreover, the angle between the surface of mesa 202 and the walls of canyon 204 is shown to be approximately 90 degrees, but this angle may be smaller or larger.

FIG. 2C is a cross-sectional view of the wet chuck illustrated in FIG. 2 taken along line C-C, which transects one of the interior canyons 204 of side 205 but does not pass through any mesas 202. Intersecting canyons 204 may be seen on side 205. Optional pin hole 249 penetrates side 205. Pin hole 249 is configured to engage with one of pins 315 of dry chuck 300, as described below with reference to FIG. 3.

FIG. 2D is a top view of side 210 of this embodiment of wet chuck 120. Openings 215 and 225 of micro-wells 130 are visible in this view.

Figures 3, 3A, 3B, 3C, 3D:
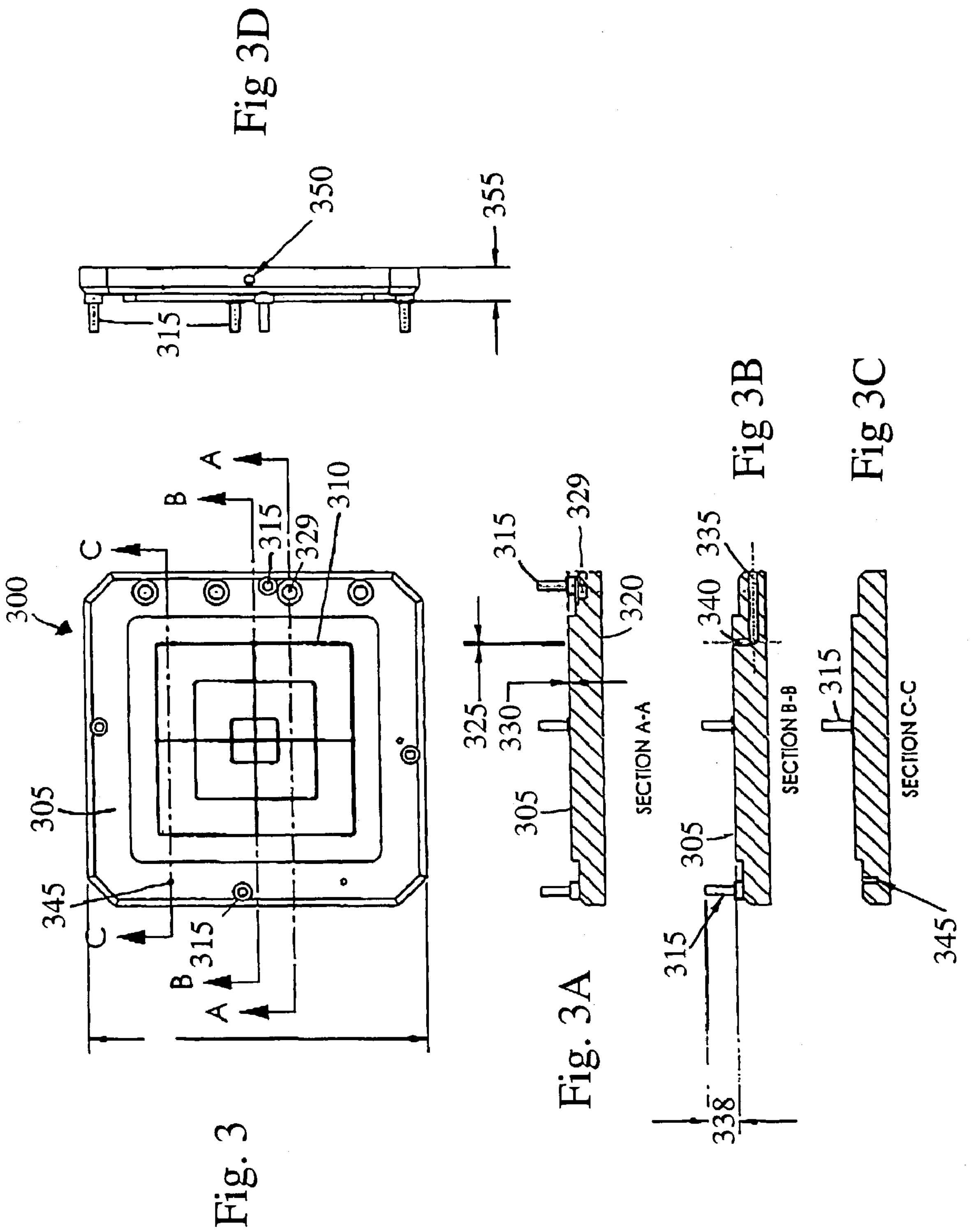
FIG. 3 is a top view of a dry chuck according to one embodiment of the invention.
FIG. 3A is a cross-section through a dry chuck according to one embodiment of the invention.
FIG. 3B is a cross-section through an air evacuation port of a dry chuck according to one embodiment of the invention.
FIG. 3C is a cross-section through a dry chuck according to one embodiment of the invention.
FIG. 3D is a side view of a dry chuck according to one embodiment of the invention.

FIG. 3 is a top view of dry chuck 300, which is configured to engage with wet chuck 120 and to retain substrate 140 in a predetermined position. Dry chuck 300 may be made of any convenient material, including but not limited to aluminum, stainless steel, plastic, acrylic, quartz and glass. In this embodiment, pins 315 of dry chuck 300 engage with pin holes 249 of wet chuck 120. However, any apparatus known in the art may be used to join dry chuck 300 and wet chuck 120, such as clamping, gluing, magnetic force, electrostatic force, gravitational force, etc. Substrate 140 may be placed in the predetermined position, for example, by aligning the edges of substrate 140 with dowel pins disposed in holes 345, or by optically aligning markings on substrate 140 with markings on dry chuck 300 or wet chuck 120. In this embodiment, side 305 includes channels 310 for retaining substrate 140 by reducing the atmospheric pressure between dry chuck 300 and substrate 140. In other embodiments, substrate 140 is retained by other means, including but not limited to gluing, acoustic welding, clamping, magnetic force or electrostatic force.

FIG. 3A depicts cross-section A-A of FIG. 3, which illustrates pins 315, base 320 and openings 329. In some embodiments, optional openings 329 provide space within which the ends of pins, screws or similar fasteners may be disposed. FIG. 3A also indicates width 325 and depth 330 of channels 310, although the scale of FIG. 3A is too small to see these features distinctly. Although channels 310 could have any convenient configuration, its dimensions are preferably kept relatively small in order to minimize the amount of air that needs to be evacuated in order to hold substrate 140 in place. In one exemplary embodiment, channels 310 have a width 325 of approximately 0.03 inches and a depth 330 of approximately 0.005 inches.

Cross-section B-B of FIG. 3 is shown in FIG. 3B. In this embodiment, pins 315 project a distance 338 from side 305. As with the other dimensions of dry chuck 300, pins 315 may be any convenient length; in one exemplary embodiment, distance 338 is approximately 0.5 inches. Ducts 335 and 340 are used to evacuate air from channels 310.

FIG. 3C depicts cross-section C-C of FIG. 3, which illustrates one of pins 315 and one of holes 345 for optional dowel pins, as described above.

FIG. 3D is a side view of this embodiment of dry chuck 300 which indicates pins 315 and opening 350 for ducts 335 and 340. Thickness 355 may be any convenient thickness; in one embodiment, thickness 355 is approximately 0.6 inches.

An alternative embodiment of the invention is shown in FIG. 4, which depicts side 205 of wet chuck 120 and base 320 of dry chuck 300. Mesas 202 and canyons 204 may be seen on side 205 of wet chuck 120. Micropipette tip 405 is shown above wet chuck 120. Substrate frame 400, an optional component of the invention, is shown engaged with dry chuck 300. Substrate frame 400 is configured to hold substrate 140, wet chuck 120 and dry chuck 300 together when liquids are added to substrate 140 through wet chuck 120. Substrate frame 400 is preferably configured to engage with a washing apparatus, such as a flow cell, to facilitate removal or washing of liquid from substrate 140. In some embodiments, this washing occurs after wet chuck 120 is removed from the apparatus and before the interaction between the liquid and the probe regions is analyzed.

Recesses 445 are formed in surface 440 of wet chuck 120. Pin 315 extends from dry chuck 300 through substrate frame 400 and engages with recesses 445 to align wet chuck 120 properly when wet chuck 120, dry chuck 300 and substrate frame 400 are assembled. Moreover, sides 450 of wet chuck 120 are configured to fit within substrate frame 400 when wet chuck 120 and substrate frame 400 are assembled. This feature may be seen more clearly with reference to FIG. 4B.

FIG. 4A indicates side 210 of wet chuck 120. Although side 210 normally includes a plurality of micro-wells 130, only one micro-well 130 is indicated on side 120 in order to more clearly indicate the location of this micro-well 130 in FIGS. 4B, 4C and 4D. Features of side 205, including mesas 202 and canyons 204, are shown in phantom. FIG. 4B illustrates cross-section B-B of FIG. 4A. Wet chuck 120 is engaged with substrate frame 400 and dry chuck 300 is engaged with substrate 140. Substrate 140 is shown as a thick line between side 205 of wet chuck 120 and side 305 of dry chuck 300, and is more clearly illustrated in FIG. 4C. Sides 450 of wet chuck 120 fit within substrate frame 400. Mesas 202 and canyons 204 of wet chuck 120 may be seen. Micropipette tip 405 is inserted into a micro-well 130 of wet chuck 120 and is in a position to dispense (or remove) a liquid. Although in this embodiment the wet chuck is shown assembled on top of the substrate, other embodiments may require a different orientation. For example, the wet chuck may be on the bottom with the mesas facing up and the substrate and dry chuck assembled above it.

FIG. 4C is an enlargement of the circled area of FIG. 4B. Accordingly, substrate 140 is more clearly visible and mesas 202, canyons 204, micropipette tip 405 and opening 215 may be more clearly seen. In this embodiment, a portion of micropipette tip 405 has an angle very close to that of angle 240. As noted above, gap 417 between wet chuck 120 and substrate 140 may vary but is preferably small: in this embodiment, gap 417 is approximately 0.005 inches.

FIG. 4D depicts micropipette tip 405 in a position to be inserted into micro-well 130 in side 210 of wet chuck 120. Pins 315 extend from dry chuck 300 through substrate frame 400. Probe arrays 100 and alleys 150 may be seen on substrate 140. Opening 350 may be seen in one side of dry chuck 300.

Figure 5:
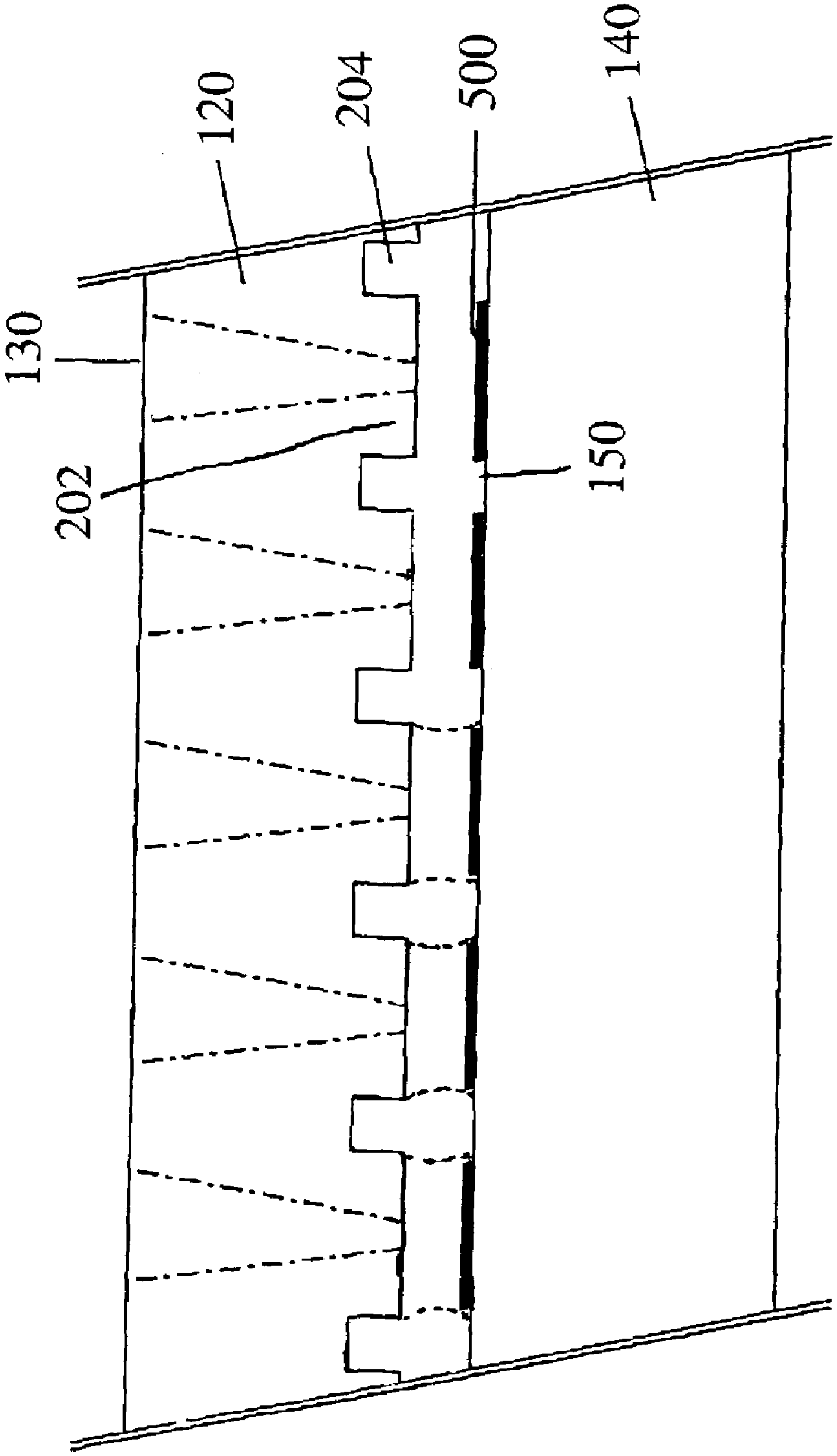
FIG. 5 is a cross-section through an assembled wafer and wet chuck according to a second embodiment of the invention.

FIG. 5 is a cross-section through another embodiment of wet chuck 120 and substrate 140. Alleys 150 of substrate 140 correspond with canyons 204 of wet chuck 120 and reaction sites 500 correspond with mesas 202. Micro-wells 130 are configured to deliver a liquid to reaction sites 500.

In some preferred embodiments, a plurality of reaction sites on substrate 140 are surrounded by a constraining region, such as a hydrophobic region, that hinders the transport of a liquid between adjacent reaction sites. Thus, the liquid in one reaction site cannot flow to other reaction sites where it could contaminate the reaction. When an aqueous or other polar reactant solution is deposited in the reaction site, it will have a relatively large wetting angle with the substrate surface so that by adjusting the amount deposited, one can ensure no flow to adjacent reaction sites. A further understanding of the nature and advantages of the boundaries herein may be understood by reference to U.S. Pat. No. 6,040,193 incorporated herein by reference. In other preferred embodiments that confine aqueous solutions, a hydrophilic material may be used to coat the mesas 202, or a hydrophobic material may be used to coat the region on the substrate surrounding the reaction sites, or both materials may be simultaneously employed. Of course, when non-aqueous or nonpolar solvents are employed, different surface coatings are generally preferred. By choosing appropriate materials (substrates, hydrophobic coatings, and solvents), the contact angle between the liquid and substrate 140 is advantageously controlled.

Figure 6:
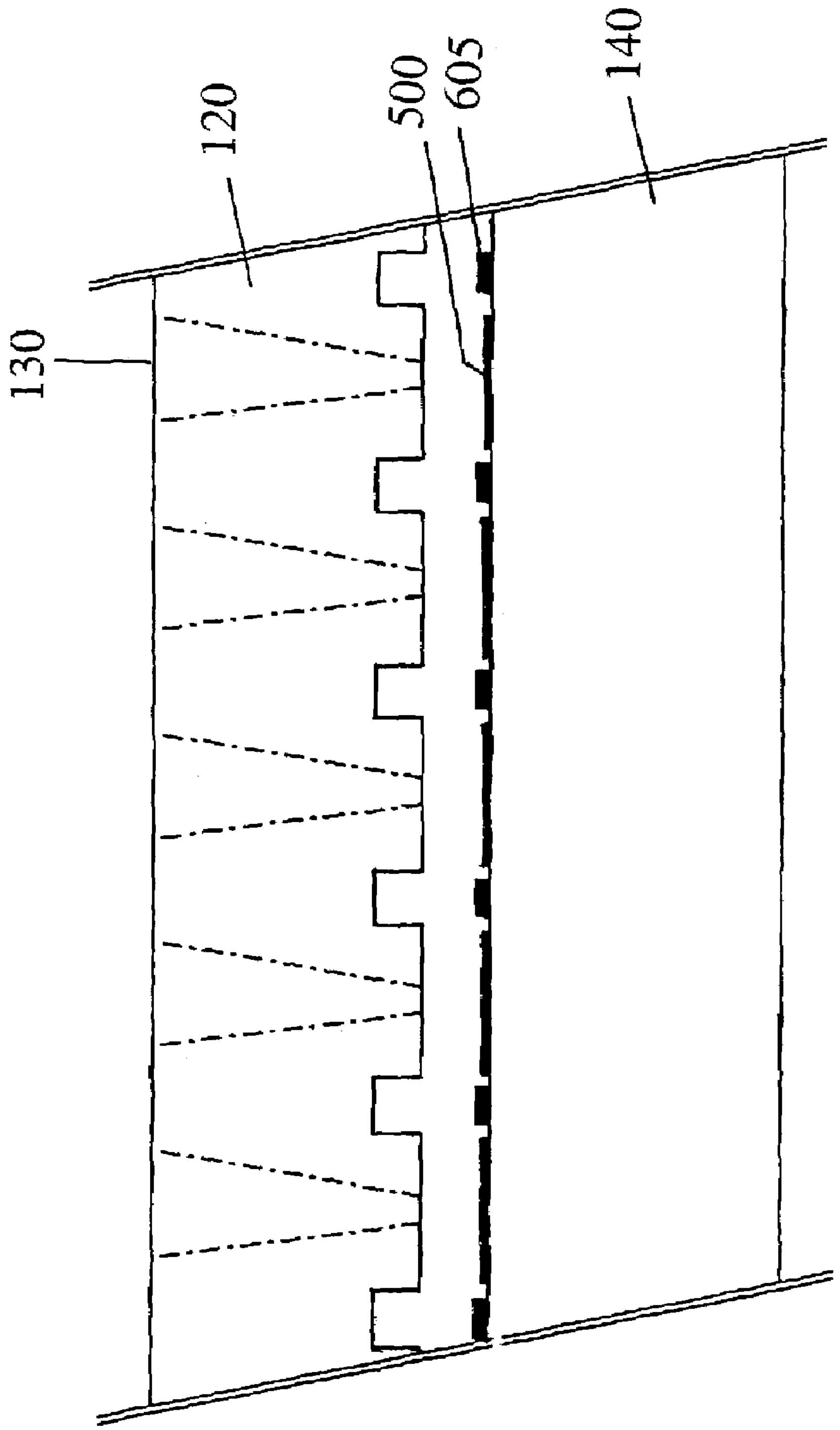
FIG. 6 is a cross-section through an assembled wafer and wet chuck according to a third embodiment of the invention.

One such embodiment is shown in FIG. 6. Hydrophobic barriers 605 are disposed between reaction sites 500. Hydrophobic barriers 605, which are resistant to the flow of an aqueous liquid, surround each reaction site 500 and help constrain liquid delivered from micro-wells 130 to each reaction site 500. Hydrophobic barriers 605 may be formed, for example, by disposing waxes, tapes or other hydrophobic materials in alleys 150 or interstitial regions 125.

In preferred methods, a liquid is introduced to each reaction site by a fluid-handling device through a micro-well 130 in wet chuck 120. The fluid-handling device adds or removes a fluid from a micro-well 130, maintains the liquid in the well at a predetermined temperature or volume, and agitates the liquid as required. Preferred embodiments and aspects of this invention employ automated fluid handling systems for concurrently performing the assay steps on each of the reaction sites. Automated fluid handling systems allows uniform treatment of liquids on the reaction sites. Microtiter robotic and other automated fluid handling systems are available commercially, for example, from Tecan AG.

Exemplary methods of precisely depositing a liquid to a specific reaction site are described in U.S. Pat. No. 6,040,193, which is incorporated herein by reference. Other deposition systems are described in the PCT application No. 99/00730 (WO 99/36760) and U.S. patent application Ser. No. 09/122,216, entitled "Depositing Fluid Specimens on Substrates, Resulting Ordered Arrays, Techniques for Analysis of Deposited Arrays," which is incorporated by reference. These references include microcapillary, ink jet and pin-and-ring dispensers, among others.

In some embodiments, a dispenser moves from one micro-well 130 to another micro-well 130, depositing only as much liquid as necessary in each. According to some such embodiments, dispensers include a micropipette to deliver a liquid to micro-well 130 and a robotic system to control the position of the micropipette with respect to wet chuck 120 and/or probe array 100. In other embodiments, micro-wells 130 are absent from wet chuck 120 and a robotic system delivers a liquid directly to sides 205 of mesas 202, then mesas 202 are placed near (or in contact with) substrate 140. In some embodiments, this robotic device is programmed to set appropriate reaction conditions (such as temperature), add liquids to the micro-wells, incubate the liquids for an appropriate time, remove unreacted liquids, wash the micro-wells and/or the substrate, add additional components as appropriate and perform detection assays. In some embodiments, the liquids are applied to the micro-wells 130 by hand, preferably with a multi-channel micropipette.

Figure 7:
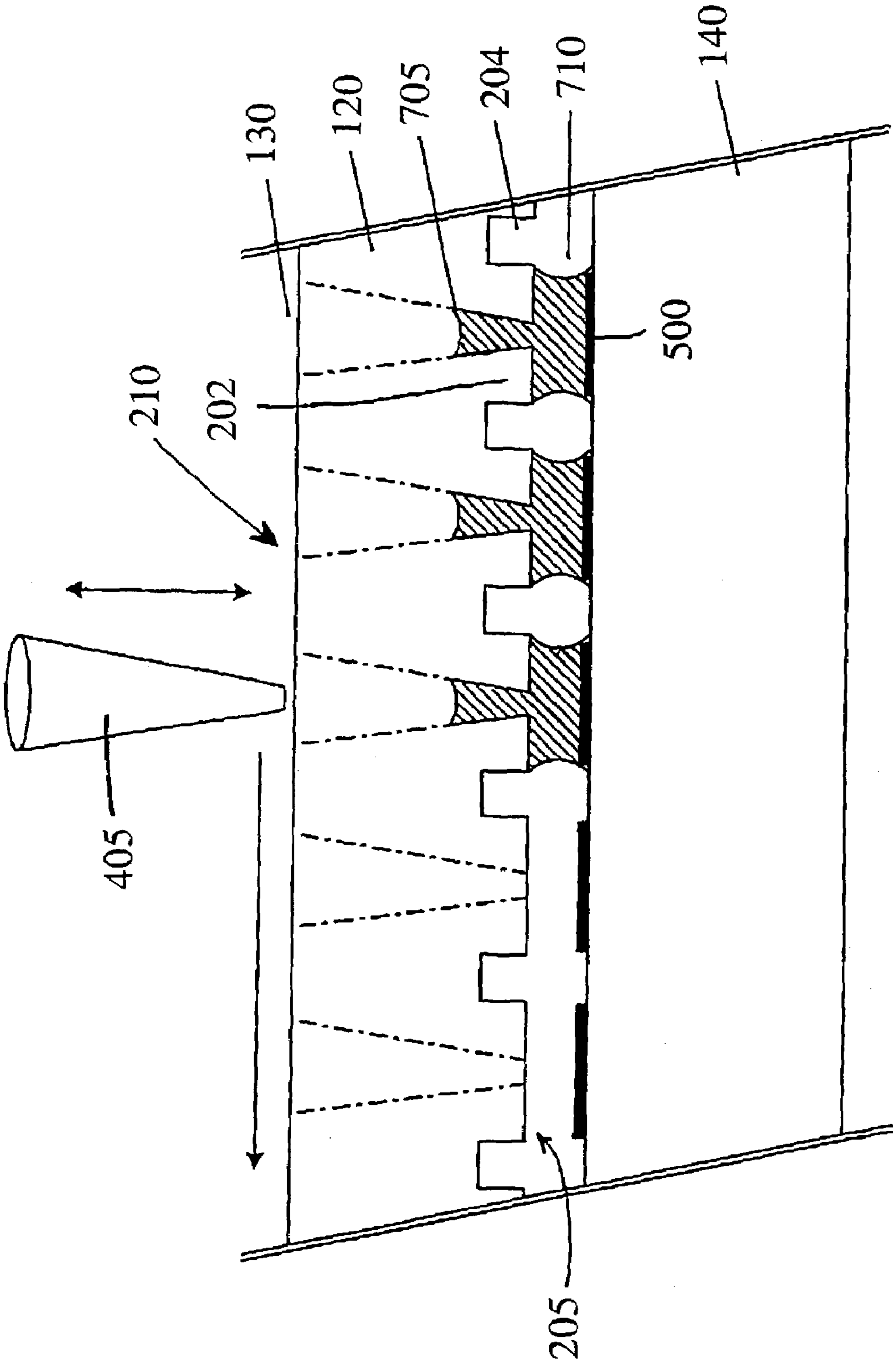
FIG. 7 is a cross-section through an assembled wafer and wet chuck to which a liquid is being applied according to one aspect of the invention.

FIG. 7 depicts in cross section one such preferred embodiment during and after the delivery of a liquid through micro-wells 130. Micropipette tip 405 of a fluid handling system delivers liquid 705 onto a reaction site 500 of substrate 140 through micro-wells 130. The liquid flows to the reaction site through capillary action, forming meniscus 710 at canyon 204. Preferably, a small reservoir of a liquid 705 is retained in each micro-well 130 to account for mixing and evaporation loss. In some embodiments, a pressure differential is applied between surfaces 205 and 210 of wet chuck 120, in order to facilitate the movement of fluid 705 to substrate 140. In some such embodiments, the pressure differential is created by evacuating some of the air from canyons 204. In some embodiments, gravity facilitates the flow of the liquid to the reaction site. In other embodiments, a force is applied by a fluid handling device to drive the fluid through the micro-well to the reaction site.

The particulars of the reaction conditions depend upon the purpose of the assay. For example, the assay may involve testing whether a liquid contains molecules that react to a probe under a specified set of reaction conditions. In this case, the reaction conditions are chosen accordingly. In other embodiments, the dispenser includes a pin and ring to deliver the liquid to the micro-well. In other embodiments, the dispenser includes a series of tubes, a manifold, an array of pipettes, or the like so that various liquids can be delivered to the probe regions, or the same liquid may be delivered to a plurality of probe regions, simultaneously.

According to some embodiments, a series of reactions may be carried out using the present invention. For example, a dispenser may deposit a first chemical entity by moving over a first probe array, dispensing a droplet into the corresponding micro-well(s), moving to a second probe array, dispensing a droplet, and so on until the each of the selected probe arrays has received an appropriate amount of the chemical entity. Next, the dispenser deposits a second chemical entity in much the same manner. In some embodiments, more than one dispenser may be used so that more than one chemical entity is simultaneously deposited. The chemical entities may react immediately on contact with a reaction site or may require a further step, such as the agitation, temperature manipulation, or addition of another chemical entity. After some number of chemical entities have been deposited and reacted in reaction sites throughout the substrate, the unreacted solution is removed from the fluid handling device by washing and optionally drying.

When a reaction is completed, an optical scanner may interrogate the probe regions of the reaction site, thereby obtaining the results of the test. Such an optical scanner is described in U.S. patent application Ser. No. 09/922,492, filed Aug. 3, 2001, entitled "High Performance Wafer Scanning", which is incorporated herein by reference in its entirety for all purposes. Gathering data from the various analysis operations, e.g., from nucleotide arrays, will typically be carried out using methods known in the art. For example, the arrays may be scanned using lasers to excite fluorescently labeled sample molecules in the liquid that have hybridized to regions of probe arrays, which can then be imaged using charged coupled devices ("CCDs") for a wide field scanning of the array. Alternatively, another particularly useful method for gathering data from the arrays is through the use of laser confocal microscopy, which combines the ease and speed of a readily automated process with high-resolution detection. Particularly preferred scanning devices are generally described in, e.g., U.S. Pat. Nos. 5,143,854, 5,424,186, 5,631,734, 5,795,716, 5,834,758, 6,025,601, 6,185,030, and PCT WO 92/10092, the teachings of which are incorporated by reference for all purposes.

Following the data gathering operation, the data will typically be reported to a data analysis operation. To facilitate the analysis operation, the data obtained by the reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probe regions, normalization of background and single base mismatch hybridizations, and the like, as described in, e.g., U.S. patent application Ser. No. 08/327,525, filed Oct. 21, 1994, and incorporated herein by reference. Other innovative computer-aided techniques for evaluating, analyzing, and processing the vast amount of information now used and made available by these pioneering technologies are disclosed in U.S. Pat. Nos. 5,733,729, 5,974164, 6,066,454, 6,013,449, 6,185,561, and 6,188,783, which are incorporated by reference for all purposes.

FIG. 8 is a schematic view of an alternative embodiment of the invention. In this embodiment, each mesa 202 includes a plurality of micro-wells 130. This embodiment is particularly desirable when a reaction site, and hence the corresponding mesa 202, is large since having multiple micro-wells 130 on a large mesa 202 would help to ensure even coverage of a liquid delivered to a reaction site. Although the mesa 202 depicted in FIG. 8 includes 104 micro-wells 130, any convenient number may be used. As described with reference to other embodiments, substrate 140 includes a plurality of probe arrays 100 separated by alleys 150. Each probe array 100 includes a plurality of probe regions 110 separated by interstitial regions 125.

III. USES

The methods of this invention will find particular use wherever high throughput of liquids is required. In particular, this invention is useful in fields impacted by the nature of molecular interaction, including chemistry, biology, genetics, medicine and diagnostics.

The present invention has many different applications in which a small amount of a liquid is transferred to a substrate. In some embodiments, the purpose for transferring the liquid to the substrate is to assay for an interaction between that a substance on the substrate and a substance in the liquid. This interaction may be hybridization, polymerization, digestion, binding, compounding, reducing, oxidizing, or any other interaction that may be detected in the laboratory. Often, tagging a substance (with radioactive or fluorescent tags, for example) in the liquid facilitates the detection of its interaction with a substance on the substrate, and vice versa. Further, the apparatus may be used to transfer more than one liquid to a particular region of a substrate, for example, for certain multi-step reactions.

In certain embodiments, the substrate may contain nucleic acid probes that correspond to specific regions of an organism's genome and the liquid may contain DNA from an individual to be compared to that on the substrate. The probes on the substrate may represent several different versions of the genome, for example, at polymorphic sites. By comparing the interaction (in general, hybridization) of the individual's DNA to the probes on the substrate, one can determine which version of the polymorphism the individual possesses in his/her genome. In some embodiments, which version of the polymorphism an individual possesses is indicative of a phenotypic trait including, but not limited to, disease resistance or susceptibility, drug response, or risk of future health problems (e.g. obesity, high blood pressure, etc.). DNA from a plurality of individuals may be simultaneously tested on a series of identical nucleic acid probe arrays on the same substrate according to the methods and apparatus of the present invention. See U.S. patent application Ser. No. 10/042,819, filed Jan. 7, 2002, entitled "Whole Genome Scanning" and U.S. patent application Ser. No. 10/152,404, filed May 21, 2002, entitled "Methods for Genomic Analysis", both of which are incorporated by reference in their entireties for all purposes.

In another embodiment of the invention, the methods and apparatus described herein are used to screen a group of substances for interactions with proteins that are contained on the substrate. Many different substances may be added to the substrate at different locations containing identical protein probe arrays to assay for interaction with the resident proteins.

A laboratory setting may require performing a single test on many patient samples. The automated methods of this invention lend themselves to these uses when the test is one appropriately performed on a substrate. For example, a DNA probe array can determine the particular strain of a pathogenic organism based on characteristic DNA sequences of the strain. The advanced techniques based on these assays now can be introduced into the clinic. A substrate may contain a plurality of a DNA probe array that can identify the pathogenic organism's strain with each probe array being a single reaction site. A liquid containing a sample from one patient may be applied to a first probe array; a liquid containing a sample from a second patient may be applied to a second probe array; and so on for all patients to be tested. In one embodiment, all liquids containing patient samples may be applied simultaneously. Once all the liquids containing patient samples are delivered to the reaction sites, the assays may be performed concurrently to determine the strain of the pathogenic organism for each patient sample.

Figure 9:
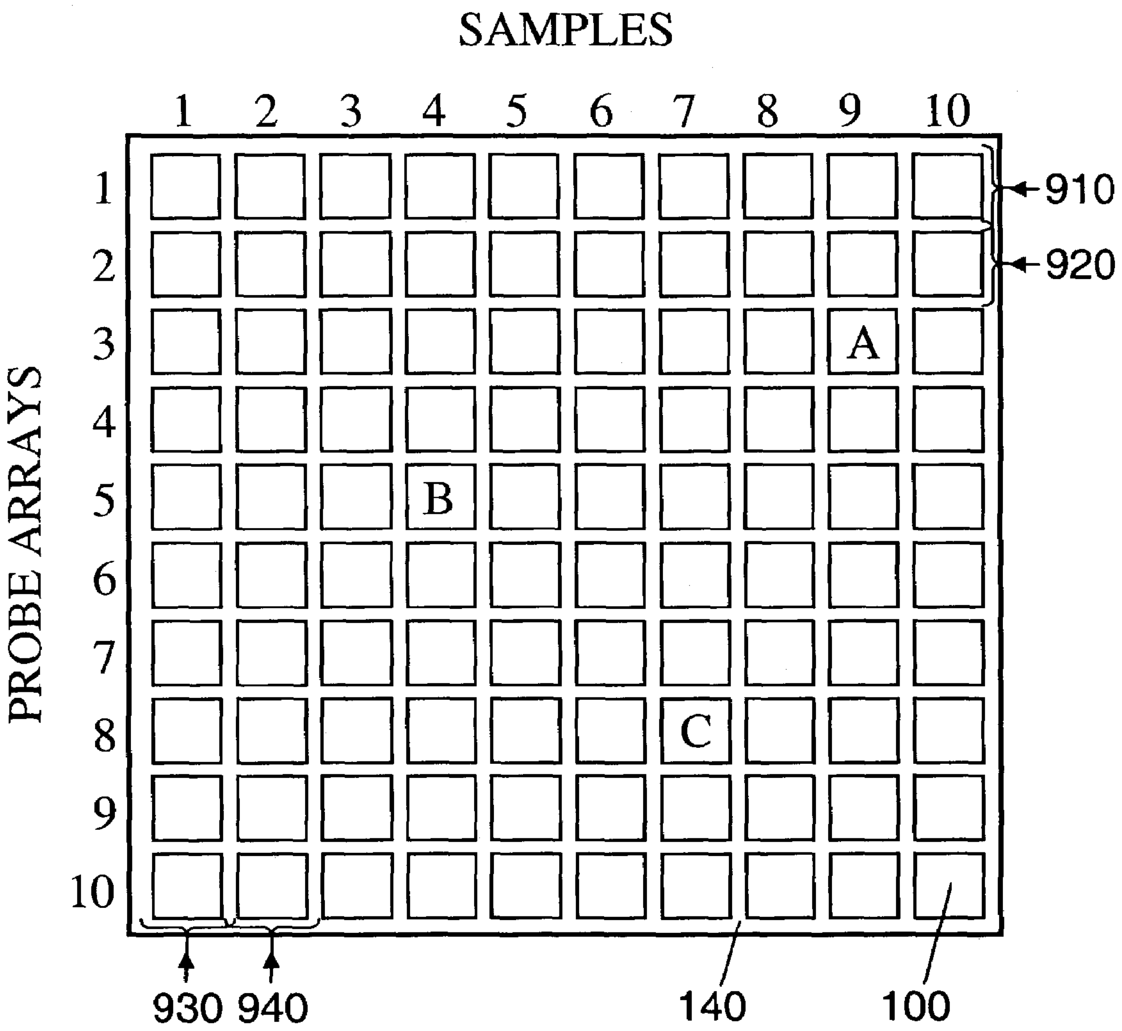
FIG. 9 depicts the layout of a substrate according to one embodiment of the invention.

FIG. 9 depicts one example of a layout of a substrate that is useful for certain methods of the invention. In some embodiments, it may be desirable to perform a plurality of tests on multiple patient samples concurrently. According to such embodiments, different areas of the substrate will contain probe arrays for diagnosis of a different disease or trait. One example is a case in which ten different samples are to be each tested on ten different probe arrays. In such a case, the substrate would preferably contain one hundred probe arrays (ten of each of the ten different probe arrays). These may be arranged on the substrate in any convenient manner. FIG. 9 shows such an embodiment in which each probe array 100 is shown as a box, and there are one hundred boxes on the substrate 140. For the purpose of simplicity, they are arranged in rows such that the first row 910 contains ten instances of a first probe array, the second row 920 contains ten of a second probe array, and so on for ten rows. The samples are applied to columns of the probe arrays 100, such that a liquid containing a first sample is applied to each of ten reaction sites in a first column 930; a liquid containing a second sample is applied to each of ten reaction sites in a second column 940; and so forth until all ten different samples have been applied to all ten different probe arrays. Thus, for example, a liquid containing a ninth sample would be added to the third variety of probe array at the position labeled "A", a liquid containing a fourth sample would be added to the fifth variety of probe array at the position labeled "B", and a liquid containing a seventh sample would be added to the eighth variety of probe array at the position labeled "C". Thus, on one substrate one hundred different assays may be run. Further, with this organization each probe array may constitute a reaction site, or a group of probe arrays to which the same sample will be applied (for example, a portion or all of column 930) may constitute a single reaction site.

Of course, this is only one simplified example as many more different probe arrays and/or samples may be utilized and arranged on a substrate according to the information sought by the practitioner of the invention, as will be clear to those skilled in the art. For example, the first row may contain probe arrays designed for a particular cancer, while other rows contain probe arrays for other cancers. Patient samples are then introduced into respective columns (or rows) of the substrate. According to some aspects of the invention, samples are introduced from a first patient in a first column of the substrate. In some aspects of this method, samples are introduced to substrate 140 through micro-wells 130 of wet chuck 120. Although the methods of the present invention are quite useful for clinical assays, they allow a level of sample complexity that is quite desirable for many other kinds of assays, as well.

In still further embodiments, relatively rarely occurring characteristics may be identified in pooled patient samples. For example, if a disease is quite rare, then samples from multiple individuals may be pooled as a first screening step in identifying the rare individual possessing the disease. To accomplish this, multiple patient samples are introduced into a single well, and for each probe array that gives a positive indication of the presence of a patient possessing the disease, each patient sample that was a part of the pool applied to that probe array is then individually processed to identify which patient exhibits that disease or trait. Thus, rather than do an initial individual screening of 10,000 patients using 10,000 probe arrays to find one individual with the disease, one could use only 100 probe arrays with 100 samples applied to each as an initial screen. Then, for a probe array that produced a "positive" result, those 100 samples would be reanalyzed individually, using another 100 probe arrays. The individual sample would thus be identified using only 200 probe arrays, rather than 10,000. The saving in time and expense would be immense.

Particular assays that will find use in automation include those designed specifically to detect or identify particular variants of a pathogenic organism, such as HIV. Assays to detect or identify a human or animal genes or polymorphisms thereof are also contemplated. In one embodiment, the assay is the detection of a human genetic variant (e.g. a single nucleotide polymorphism, or SNP) in an individual DNA or a pool of DNA molecules collected from a given population that indicates existence of or predisposition to a genetic disease or other phenotypic trait of interest, either from acquired or inherited mutations. These include, but are not limited to genetic diseases such as cystic fibrosis, diabetes, and muscular dystrophy, as well as diseases such as cancer (the P53 gene is relevant to some cancers), as disclosed in U.S. patent application Ser. No. 08/143,312, which is incorporated herein by reference in its entirety for all purposes.

The present invention provides a novel apparatus and method for performing assays on a substrate. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

The invention claimed is:

1. An apparatus for constraining a liquid to a selected area of a substrate, said apparatus comprising:

a dry chuck for retaining the substrate; and a wet chuck having a first side configured to receive the liquid and constrain the liquid to the selected area of the substrate, wherein said first side comprises a hydrophilic raised portion that positions the liquid on the selected area of the substrate, and grooves surrounding said hydrophilic raised portion, the surface of the grooves being hydrophobic, wherein said hydrophilic raised portion is raised relative to said grooves, and further wherein the first side of the wet chuck is configured to constrain the liquid to the selected area of the substrate without the use of a means for contacting the substrate contained within the grooves.

2. The apparatus of claim 1, wherein said dry chuck and said wet chuck are configured to maintain a gap between said substrate and said raised portion of said wet chuck when the chucks are assembled together.

3. The apparatus of claim 1, wherein said wet chuck has a second side comprising at least one channel that extends from said second side to said raised portion on said first side.

4. The apparatus of claim 3 wherein said at least one channel is used to deliver said liquid to said selected area of said substrate.

5. The apparatus of claim 3, wherein said at least one channel is used to deliver said liquid to a gap between said at least one raised portion on said first side and said selected area of said substrate.

6. The apparatus of claim 4 or 5, wherein the flow of said liquid through said at least one channel is facilitated by capillary action, gravity flow, or a pressure differential.

7. The apparatus of claim 3, said apparatus further comprising a manual or automated fluid-handling device, wherein said at least one channel is configured to receive said liquid from said manual or automated fluid-handling device.

8. A method for simultaneously constraining a plurality of liquids to selected regions of a substrate, the method comprising the steps of:

a) providing the apparatus of claim 1;

b) dispensing a first liquid on a first raised portion of the wet chuck;

c) dispensing a next liquid on a next raised portion of the wet chuck;

d) repeating step c) until a plurality of liquids have been dispensed on separate raised portions of the wet chuck; and e) placing the raised portions in proximity to the selected regions of the substrate, thereby wetting the selected regions of the substrate with the liquids and constraining the liquids to the selected regions of the substrate.

9. A method for constraining a first liquid to a first area of a substrate and a second liquid to a second area of the substrate, said method comprising the steps of:

providing the apparatus of claim 1;

dispensing the first liquid through a first channel in the first side of the wet chuck to a first raised portion of a second side of the wet chuck;

dispensing the second liquid through a second channel in the first side of the wet chuck to a second raised portion of the second side of the wet chuck;

constraining the first liquid to the first area of the substrate by holding the first raised portion of the second side of the wet chuck in proximity to the first area of the substrate; and constraining the second liquid to the second area of the substrate by holding the second raised portion of the second side of the wet chuck in proximity to the second area of the substrate.

10. The method of claim 9, wherein the dispensing steps comprise using a fluid-handling system configured to deposit the first liquid in the first channel of the wet chuck and the second liquid in the second channel of the wet chuck.

11. The apparatus of claim 1, wherein the liquid is comprised of substances selected from the group consisting of nucleic acids, peptides, polysaccharides, phospholipids, hybrid polymers, glycoproteins, inorganic compounds, proteins, peptides, antibodies, carbohydrates, acids, bases, salts, compounds, buffers and solvents.

* * * * *